United States Patent [19]

Verdicchio

[11] Patent Number: 4,587,266

[45] Date of Patent: May 6, 1986

[54] ANTIMICROBIAL COMPOSITIONS

[75] Inventor: Robert J. Verdicchio, Succasunna, N.J.

[73] Assignee: Johnson & Johnson Baby Products Company, New Brunswick, N.J.

[21] Appl. No.: 664,287

[22] Filed: Oct. 24, 1984

Related U.S. Application Data

[63] Continuation-in-part of Ser. No. 423,379, Sep. 24, 1982, abandoned.

[51] Int. Cl.$^4$ ..................... A01N 37/52; A01N 33/24; C11D 3/48
[52] U.S. Cl. .................................... 514/635; 514/644; 252/106
[58] Field of Search ................ 424/320; 514/644, 635; 252/106

[56] References Cited

U.S. PATENT DOCUMENTS

| | | | |
|---|---|---|---|
| 3,976,765 | 8/1976 | Nachtigal | 424/54 |
| 4,145,436 | 3/1979 | Michaels | 424/320 |
| 4,150,114 | 4/1979 | Smith | 424/59 |
| 4,183,952 | 1/1980 | Michaels | 424/320 |

OTHER PUBLICATIONS

McCutcheon's *Detergents & Emulsifiers,* 1973 N. Amer. Edition pp. 16, 35 and 41.

*Primary Examiner*—Jerome D. Goldberg
*Assistant Examiner*—Freda Abramson
*Attorney, Agent, or Firm*—Steven P. Berman

[57] ABSTRACT

Antimicrobial compositions comprising a bis-biguanide compound and an amidoamine oxide.

6 Claims, No Drawings

ANTIMICROBIAL COMPOSITIONS

CROSS REFERENCE TO RELATED APPLICATIONS

This is a continuation-in-part of application Ser. No. 423,379, filed Sept. 24, 1982, now abandoned.

BACKGROUND OF THE INVENTION

The present invention relates to compositions useful as antimicrobial agents. More particularly, it relates to the enhancement of the activity of specific bis-biguanide antimicrobial compounds by the addition of amine oxides.

Numerous antimicrobial agents and compositions have been described in the literature and these compounds have attained widespread utility, for example, as preservatives in the cosmetic and pharmaceutical area as well as for cleansing purposes. Such compositions to be useful should demonstrate high activity against a wide range of organisms while exhibiting low toxicity as well as being free from odor, easily handled and chemically stable. When such compositions are effective against bacteria, they are also referred to as antibacterial compositions. Notwithstanding the widespread acceptance of such compositions, there is an ongoing search for more effective antimicrobial agents and compositions and, therefore, there is a need to enhance the antimicrobial activity of known antimicrobial agents by the addition of other compounds.

One of the objects of the present invention is to provide a method of enhancing the antimicrobial effect of compounds having known antimicrobial activity.

Another object of this invention is to provide an antimicrobial composition comprising one or more antimicrobial compounds in combination with a compound which enhances the antimicrobial activity of the antimicrobial compound.

A still further object of this invention is to provide antibacterial compositions effective against both gram positive bacteria and gram negative bacteria.

These and other objects of the invention will become apparent from the following description.

SUMMARY OF THE INVENTION

In accordance with the present invention, there is provided compositions useful as antimicrobial agents comprising (A) a bis-biguanide compound selected from the group consisting of polyhexamethylene biguanide hydrochlorides and chlorhexidine salts, and (B) an amidoamine oxide.

The enhancing effect on the antimicrobial properties is most remarkable when component (A) is employed with component (B) within specific ratios and the compositions of the invention can be employed as antimicrobial agents in various personal care products.

DETAILED DESCRIPTION

There are employed as the bis-biguanide compound, a compound selected from the group consisting of polyhexamethylene bis-biguanide hydrochlorides of the formula:

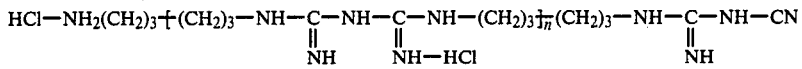

wherein n is from 4.5 to 6.5; and chlorhexidine salts of 1,6-di-(4-chlorophenylbiguanide)-hexane of the formula:

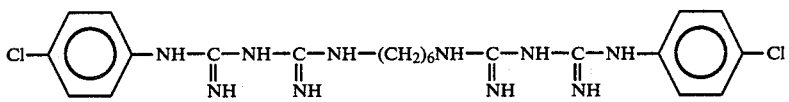

The salts which are useful include chlorhexidine acetate, chlorhexidine hydrochloride and chlorhexidine gluconate. These compounds may be employed alone or in mixtures.

The polyhexamethylene biguanide hydrochlorides are available commercially, for example, from ICI Americas Inc. Wilmington, Del. under the tradename Cosmocil CQ and the chlorhexidine salts are also available commercially, for example, the chlorhexidine gluconate from ICI Americas Inc., Wilmington, Del. under the tradename, Chlorhexidine. The bis-biguanides should be present in the compositions of the present invention from about 2 to 5% by weight of the total composition, preferably from about 3 to 4%.

The amine oxides which are useful in the compositions of the present invention are the amidoamine oxides of the formula:

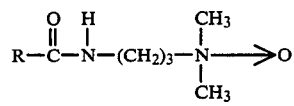

wherein R is straight chain alkyl of from 7 to 17 carbon atoms or mixtures thereof.

The amidoamine oxides are available commercially, for example, from Lonza Chemical Company, Fairlawn, N.J. under the tradename Barlox C and from Onyx Chemical Company, Jersey City, N.J. under the tradename Ammonyx CDO. Barlox C and Ammonyx CDO are cocoamidopropyldimethyl amine oxides. The amidoamine oxides should be present in the compositions of the present invention from about 1 to 20% by weight of the total composition, preferably from about 4 to 8%.

In order to obtain the desired results of the present invention the amidoamine oxide to bis-biguanide ratio should be from about 1:2 to 4:1, preferably about 1:1. If the ratio is less than about 1:2 the enhancement effect of the amidoamine oxide begins to diminish and if the ratio is greater than about 4:1, the resulting compositions tend to become harsh to the user and also are relatively expensive.

The balance of the compositions consist of water and may also contain minor amounts of other components normally found in such compositions such as chelating agents, thickening agents, fragrances, coloring agents and the like.

The pH of the compositions should be maintained within a range of from about 4 to 8, preferably 7.0 to 7.5.

The present invention is more particularly described and explained by means of the following examples:

EXAMPLE I

An antimicrobial composition is prepared as follows: a Methocel (hydroxypropylmethyl cellulose) solution containing 1.9 g. active sufficient to provide 0.75% w/w Methocel in the finished product is added to 75 g. deionized water and mixed until homogeneous. To this solution is added 50 g. of a 20% active polyhexamethylene biguanide hydrochloride sold under the tradename Cosmocil CQ by ICI Americas Inc., Wilmington, Del., followed by the addition of 0.25 g. Versene 100 and 16.75 g. of 30% active cocoamidopropyldimethyl amine oxide. The pH is adjusted to 6.0 using 15% HCl and the total is adjusted to 250 g. by the addition of deionized water. The resulting composition is of the following formula:

|  | % w/w |
|---|---|
| Cosmocil CO | 4.00 |
| Versene 100 (tradename of Dow Chemical Company for the sodium salt of ethylenediaminetetraacetic acid) | 0.10 |
| hydroxypropylmethyl cellulose | 0.75 |
| cocoamidopropyldimethyl amine oxide | 2.00 |
| deionized water qs to | 100 |

EXAMPLE II

An antimicrobial composition is prepared according to the procedure of Example I except that cocoamidopropyldimethyl amine oxide is eliminated and replaced with deionized water.

EXAMPLE III

An antimicrobial composition is prepared according to the procedure of EXAMPLE I except that Cosmocil CQ is eliminated and replaced with deionized water.

EXAMPLE IV

An antimicrobial composition is prepared according to the procedure of Example I except that 33.25 g. of cocoamidopropyldimethyl amine oxide are utilized resulting in a 1:1 ratio of amine oxide to Cosmocil CQ (on an "actives" basis).

EXAMPLE V

An antimicrobial composition is prepared according to the procedure of Example I except that 66.6 g. of amine oxide are utilized resulting in a 2:1 ratio of amine oxide to Cosmocil CQ (on an "actives" basis).

EXAMPLE VI

A screening technique is used to test the compositions in Examples I-V. This technique consists of preparing 2-fold or 4-fold serial dilutions of the compositions of each Example. Aliquots of these dilutions are then inoculated with a mixed suspension of gram positive bacteria or a mixed suspension of gram negative bacteria. The inoculm density is adjusted to yield approximately $10^7$ bacteria/ml of sample. Portions of the inoculated sample are then tested for viable bacteria at zero-time (immediately after inoculation), 6 to 8 minutes, 15 minutes, 30 minutes and 60 minutes after inoculation. This testing involves placing a calibrated 0.01 ml transfer loop into the inoculated sample and removing a premeasured portion which is then streaked on a solid growth medium (agar) and incubated for a period of 48 hours at a temperature of 35° C. After the incubated period, the plates are examined for the presence or absence of growth. Any amount of growth on the line of streak is considered as positive growth. When the compositions of Examples I-V are tested according to the above procedure the following results are obtained. These results are expressed in tems of the minimum inhibitory concentration required for complete kill expressed in micrograms per milliliter (mcg/ml).

TABLE I

| Composition | Gram Positive time(minutes) | | | | | Gram Negative 8 time(minutes)v | | | | |
|---|---|---|---|---|---|---|---|---|---|---|
|  | 0 | 6–8 | 15 | 30 | 60 | 0 | 6–8 | 15 | 30 | 60 |
| Example I | $>10^4$ | $10^4$ | 156 | 39 | <19 | 2500 | 312 | 39 | <19 | <19 |
| Example II | $>10^4$ | 5000 | 625 | 78 | 156 | 2500 | 39 | <19 | <19 | <19 |
| Example III | $>10^4$ | $>10^4$ | 5000 | 1250 | 1250 | $>10^4$ | $>10^4$ | $>10^4$ | $>10^4$ | $>10^4$ |
| Example IV | $>10^4$ | 625 | 19 | <19 | <19 | 625 | <19 | <19 | <19 | <19 |
| Example V | $>10^4$ | 1250 | 19 | <19 | <19 | 5000 | <19 | <19 | <19 | <19 |

These results clearly demonstrate the antimicrobial advantages of the compositions of the present invention, i.e., the compositions of Examples I, IV and V.

EXAMPLE VII

An antimicrobial composition is prepared according to the procedure of Example I and is of the following formulation:

|  | % wt/wt |
|---|---|
| Chlorhexidine gluconate | 4.00 |
| Versene 100 | 0.10 |
| hydroxypropylmethyl cellulose | 0.75 |
| cocoamidopropyldimethyl amine oxide | 4.00 |
| deionized water qs to | 100 |

The pH of the above formulation is adjusted to 6.0 with dilute HCl.

EXAMPLE VIII

An antimicrobial composition is prepared according to the procedure of Example VII except that the cocoamidopropyldimethyl amine oxide is utilized in a 1:2 ratio of amine oxide to chlorhexidine gluconate (on an "actives" basis).

EXAMPLE IX

An antimicrobial composition is prepared according to the procedure of Example VII except the cocoamidopropyldimethyl amine oxide is eliminated and replaced with deionized water.

EXAMPLE X

An antimicrobial composition is prepared according to the procedure of EXAMPLE VII except the chlorhexidine gluconate is eliminated and replaced with deionized water.

EXAMPLE XI

The compositions of Examples VII, VIII, IX and X are tested according to the procedure of Example VI and give the following results.

TABLE II

| Composition | Gram Positive time(minutes) | | | | | Gram Negative time(minutes) | | | | |
|---|---|---|---|---|---|---|---|---|---|---|
| | 0 | 6–8 | 15 | 30 | 60 | 0 | 6–8 | 15 | 30 | 60 |
| Example VII | >2500 | 19 | 19 | 19 | 19 | 625 | 39 | 19 | 10 | 10 |
| Example VIII | >2500 | 625 | 39 | 39 | 39 | 2500 | 78 | 39 | 19 | 39 |
| Example IX | >2500 | 2500 | 2500 | 2500 | 625 | >2500 | 39 | 39 | 39 | 19 |
| Example X | >2500 | >2500 | >2500 | >2500 | >2500 | >2500 | >2500 | >2500 | >2500 | >2500 |

Various other features and embodiments of the present invention not specifically set forth will be obvious to those skilled in the art, all of which may be achieved without departing from the spirit and scope of the invention as defined by the following claims.

What is claimed is:

1. An antibacterial composition, comprising as the active ingredients (a) a bis-biguanide compound of the formula

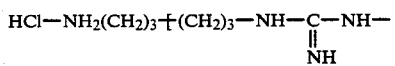
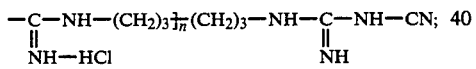

wherein n is from 4.5 to 6.5; or chlorhexidine salts selected from the group consisting of chlorhexidine acetate, chlorhexidine hydrochloride and chlorhexidine gluconate; and (b) an amidoamine oxide of the formula

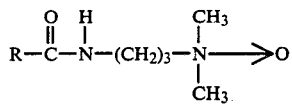

wherein R is straight chain alkyl of from 7 to 17 carbon atoms or mixtures thereof and wherein the amidoamine oxide and bis-biguanide compound are present in a weight ratio of about 1:1.

2. The composition of claim 1 wherein the bis-biguanide compound is a polyhexamethylene biguanide of the formula

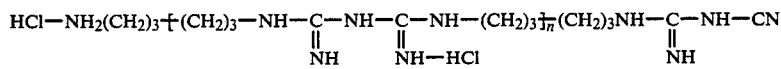

wherein n is from 4.5 to 6.5.

3. The composition of claim 1 wherein the bis-biguanide compound is chlorhexidine acetate.

4. The composition of claim 1 wherein the bis-biguanide compound is chlorhexidine hydrochloride.

5. The composition of claim 1 wherein the bis-biguanide compound is chlorhexidine gluconate.

6. The composition of claim 1 wherein the amidoamine oxide is cocoamidopropyldimethyl amine oxide.

* * * * *